United States Patent [19]

Ishiguro et al.

[11] Patent Number: 4,835,009
[45] Date of Patent: May 30, 1989

[54] METHOD OF PRODUCING OXYGEN SENSING ELEMENT

[75] Inventors: Fujio Ishiguro; Takumi Narahara, both of Nagoya, Japan

[73] Assignee: NGK Insulators, Ltd., Japan

[21] Appl. No.: 134,985

[22] Filed: Dec. 18, 1987

[30] Foreign Application Priority Data

Dec. 27, 1986 [JP] Japan ............................ 61-311195

[51] Int. Cl.[4] ............................................. B05D 5/12
[52] U.S. Cl. .................................. 427/126.2; 427/126.3; 427/126.5; 427/199; 427/376.2
[58] Field of Search ............... 427/126.2, 126.5, 126.3, 427/199, 376.2

[56] References Cited

U.S. PATENT DOCUMENTS

| | | |
|---|---|---|
| 3,607,433 | 9/1971 | Isenberg et al. |
| 4,175,019 | 11/1979 | Murphy .............................. 204/429 |
| 4,294,679 | 10/1981 | Maurer .............................. 29/592 R |
| 4,296,148 | 10/1981 | Friese .............................. 427/126.2 |
| 4,334,974 | 6/1982 | Muller .............................. 204/426 |
| 4,359,374 | 11/1982 | Sano et al. |
| 4,402,820 | 9/1983 | Sano .............................. 204/429 |
| 4,421,787 | 12/1983 | Ikezawa .............................. 427/126.2 |
| 4,477,487 | 10/1984 | Kojima et al. .............................. 427/123 |
| 4,505,807 | 3/1985 | Yamada .............................. 427/126.5 |
| 4,530,751 | 7/1985 | Ishiguro .............................. 427/126.2 |
| 4,650,697 | 3/1987 | Kitagawa .............................. 427/126.2 |
| 4,668,375 | 5/1987 | Kato .............................. 204/426 |

*Primary Examiner*—Shrive Beck
*Assistant Examiner*—Vi Duong Dang
*Attorney, Agent, or Firm*—Arnold, White & Durkee

[57] ABSTRACT

A method of producing an oxygen sensing element including a main body made of an oxygen-ion conductive solid electrolyte, an undulated layer formed on the main body, a measuring electrode formed on the undulated layer for exposure to a measurement gas, and a porous protective coating which covers the measuring electrode. A solid electrolyte material having a higher degree of sinterability than the oxygen-ion conductive solid electrolyte of the main body of the sensing element is prepared, to form an unfired layer for the undulated layer on a selected portion of an unfired body for the main body. The formed unfired layer for the undulated layer is fired together with the unfired body for the main body, under firing conditions selected for the unfired body, whereby the undulated layer is formed as an integral part of the main body of the sensing element.

6 Claims, 5 Drawing Sheets

METHOD OF PRODUCING OXYGEN SENSING ELEMENT

BACKGROUND OF THE INVENTION

1. Field of the Invention

The present invention relates generally to a method for producing a sensing element of an oxygen sensor, and more particularly to a method suitable for fabricating the sensing element so as to improve the operating response of the oxygen sensor, and the adhesion of an undulated layer to a solid electrolyte main body of the sensing element.

2. Discussion of the Prior Art

In the art of controlling an air/fuel (A/F) ratio of an air-fuel mixture for an internal combustion engine for automotive vehicles or other applications, it is known to detect the oxygen concentration of exhaust gases emitted by the engine, by a sensor which uses an oxygen-ion conductive solid electrolyte such as zirconia ceramics. The sensor is operated according to the principle of an oxygen concentration cell.

Such an oxygen sensor for detecting the oxygen concentration employs a sensing element which includes a tubular solid electrolyte body which is closed at one of its opposite ends and open at the other end. The solid electrolyte body has an inner and an outer electrode on its respective inner and outer surfaces. The inner electrode serves as a reference electrode which is exposed to an ambient air as a reference gas having a known oxygen concentration. On the other hand, the outer electrode serves as a measuring electrode which is exposed to a measurement gas in the form of the exhaust gases emitted by an internal combustion engine. According to this oxygen sensor, the concentration of oxygen in the exhaust gases is determined by measuring an electromotive force that is induced between the reference and measuring electrodes, based on a difference in the oxygen concentration between the reference gas and the measurement gas.

In a known oxygen sensor of the type described above, an oxygen-ion conductive solid electrolyte constitutes a suitably shaped main body of the oxygen sensing element, on which the electrodes are formed in contact with the surfaces of the solid electrolyte. In operation, the oxygen sensor is subject to heat of the exhaust gases having a generally high temperature. Consequently the measuring electrode tends to suffer from separation or peel-off from the surface of the solid electrolyte main body, and the sensing capability or measuring accuracy of the oxygen sensor is deteriorated. To solve this problem, U.S. Pat. No. 4,477,487 and German Pat. No. 3118299 propose a technique to improve the adhesive strength between the main body and the measuring electrode, by disposing the measuring electrode on an undulated outer layer of a solid electrolyte formed as an integral outer part of the main body of the sensing element. In order to improve the durability or life expectancy of the measuring electrode, a porous ceramic protective coating is formed on the measuring electrode to protect it from exposure to the exhaust gases.

The undulated outer solid electrolyte layer indicated above is applied to a suitable area on the outer surface of the prepared solid electrolyte main body of the oxygen sensing element, by spraying, dipping or other suitable methods. Subsequently, the formed undulated outer layer is fired into an integral outer covering of the sensing element. Since the density of the unfired solid electrolyte material of the undulated outer layer is lower than that of the solid electrolyte of the pre-formed main body of the sensing element, the fired undulated outer layer tends to have many open pores or voids, in which there exists an atmosphere in an exhaust pipe connected to an engine while the engine is not in operation. When exhaust gases are emitted from the engine and the oxygen sensor is exposed to the exhaust gases, the atmosphere in the open pores is only gradually replaced or interchanged by the exhaust gases in the exhaust pipe. Namely, the replacement or interchange of the atmosphere in the pores takes a relatively long time, and the oxygen sensor suffers from a deteriorated operating response, i.e., increased response time of the sensor output (electromotive force) to a change in the oxygen concentration (oxygen partial pressure) of the exhaust gases as a measurement gas.

SUMMARY OF THE INVENTION

It is therefore an object of the present invention to provide a method suitable for producing a sensing element of an oxygen sensor having an undulated layer formed on the surface of its main body, which method permits the formation of the undulated layer so as to have a dense structure, thereby improving the operating response of the sensor.

Another object of the invention is to provide such a method of producing the sensing element, which ensures improvements in adhesive strength between the undulated layer, and an electrode and a protective coating formed on the undulated layer, strength of the main body of the sensing element, and adhesive strength between the undulated layer and the main body of the sensing element.

The above objects may be attained according to the principle of the present invention, which provides a method of producing a sensing element of an oxygen sensor which includes a main body made of an oxygen-ion conductive solid electrolyte, an undulated layer formed on the main body, a measuring electrode formed on the undulated layer for exposure to a measurement gas, and a porous protective coating which covers the measuring electrode, the method comprising the steps of: preparing a solid electrolyte material which has a higher degree of sinterability than the oxygen-ion conductive solid electrolyte of the main body of the sensing element; forming an unfired layer for the undulated layer on a selected portion of an unfired body for the main body, by using the prepared solid electrolyte material; determining firing conditions for the unfired body for the main body; and firing the formed unfired layer for the undulated layer, together with the unfired body for the main body, under the determined firing conditions, to thereby produce the oxygen sensing element which has the undulated layer as an integral part of the main body.

According to the method of the invention described above, the undulated layer is formed of a solid electrolyte which has better sinterability than that of the main body of the oxygen sensing element. The unfired layer for the undulated layer, and the unfired body for the main body of the sensing element are co-fired under the same conditions, whereby a fired integral mass of the sensing element is produced. The instant method permits the obtained undulated layer to have a dense structure which is substantially free of undesirable open pores as encountered in the conventional sensing element.

While the main body and the undulated layer of the sensing element may be formed from various known oxygen-ion conductive solid electrolyte materials, these main body and undulated layer may preferably be formed of a fully or partially stabilized zirconia ceramic which includes a suitable stabilizer such as yttria ($Y_2O_3$), calcia (CaO), magnesia (MgO), or ytterbium oxide ($Yb_2O_3$).

As known in the art, the solid electrolyte materials for the sensing element usually contain suitable sintering aids, for example, kaoline or other clays, $SiO_2$, $Al_2O_3$, and $Fe_2O_3$.

The solid electrolyte material used for the undulated layer according to the present invention demonstrates a higher degree of sinterability than that for the main body of the sensing element. That is, the material for the undulated layer is selected so that the material can be sintered at a lower temperature than that for the main body. The following techniques are available to change or adjust the sinterability of the solid electrolyte material:

Namely, the sintering temperature of the unfired layer for the undulated layer of the sensing element can be lowered by using (a) a solid electrolyte material whose average or mean particle size is smaller than that of the solid electrolyte of the main body, (b) a solid electrolyte material in the form of a dry-crushed powder, or (c) a zirconia ceramic which contains a smaller content of stabilizer than the solid electrolyte of the main body. The sinterability of the solid electrolyte material for the undulated layer may also be improved by increasing the content of sintering aids included in the material. Further, it is noted that the sintering temperature of the solid electrolyte of the main body can be raised by lowering a forming pressure applied to the material when the unfired mass for the main body is formed under pressure, for example, on a rubber press or cold isostatic press. In other words, the sintering temperature of the solid electrolyte material for the undulated layer may be lowered with respect to the sintering temperature of the main body, by lowering the forming pressure of the main body. The techniques indicated above are selectively used, either alone or in suitable combination.

With the above considerations given in selecting the solid electrolyte for the main body of the oxygen sensing element, the selected solid electrolyte is formed into a desired tubular shape in a suitable known process such as press molding by using a rubber press, for example, as indicated above. Thus, a tubular unfired body for the main body of the oxygen sensing element is obtained.

The unfired main body of the sensing element is calcined if and as needed. Subsequently, an unfired layer for the undulated layer is formed in a suitable area on the outer surface of the unfired or calcined main body, with the selected solid electrolyte material indicated above. A suitable known technique, such as spraying or dipping method, is practiced to form the unfired undulated layer. The thickness, undulation, and other parameters of the layer may be determined to meet the specific requirements of each sensor.

The unfired or calcined main body and the unfired undulated layer formed thereon are co-fired under the conditions which are selected for firing the main body. As a result, the fired structure including the undulated layer as an integral part of the main body is prepared.

Described more specifically, the unfired undulated layer formed of the solid electrolyte material which has better sinterability than that of the main body can be sintered during or before the sintering of the unfired or calcined main body, because the co-firing conditions are determined so that the unfired main body is eventually sintered. Consequently, the fired undulated layer may be given a comparatively dense structure which does not have undesirable open pores which would otherwise be encountered. The thus increased density of the undulated layer results in an increase in the strength of the main body of the sensing element, and an increase in the adhesive strength between the main body and the undulated layer.

On the thus prepared fired structure consisting of the main body and the outer undulated layer, there are formed at least a reference electrode and a measuring electrode, in a suitable manner as commonly practiced in the art, for instance, by plating, sputtering, thermal decomposition of salts of the electrode metal, or firing of an applied paste of the electrode metal. At least the measuring electrode is formed on the outer undulated layer of the sensing element, in the form of a thin film of a conductive material. The electrodes may be formed of a metal selected from the platinum group which includes platinum, ruthenium, osmium, iridium, rhodium and palladium, or alternatively formed of a conductive material whose principal component is selected from the platinum group.

After the measuring electrode is thus formed on the undulated layer of the sensing element, a porous ceramic protective coating having a suitable thickness is applied so as to cover the measuring electrode, for improving the durability of the measuring electrode. While this ceramic protective coating may be formed in one of various known methods, a generally practiced method is to use a plasma- or flame-spray coating technique. In particular, the plasma-spray coating is preferred. In this method, a selected ceramic material, usually spinel ($Al_2O_3.MgO$), is sprayed on the measuring electrode, by means of $Ar/N_2$ or $N_2/H_2$ plasma flame, so as to form a desired ceramic protective coating having a porous structure.

The thus formed ceramic protective coating covering the measuring electrode has an effectively increased adhesive strength with respect to the main body of the sensing element, in the presence of the dense structure of the undulated layer. The thus prepared oxygen sensing element which posseses excellent characteristics is incorporated into an oxygen sensor.

BRIEF DESCRIPTION OF THE DRAWINGS

The above and other objects, features and advantages of the present invention will be better understood by reading the following detailed description of the invention, when considered in connection with the accompanying drawings, in which.

DETAILED DESCRIPTION OF THE INVENTION

Figure 1A:
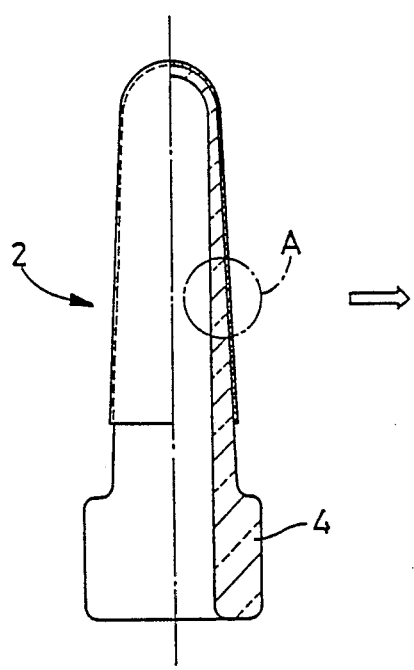
FIG. 1(a) is an elevational view partly in longitudinal cross section of an oxygen sensing element prepared according to one embodiment of the present invention.

Referring first to FIG. 1(a), the sensing element of an oxygen sensor manufactured according to one embodiment of a method of the present invention is indicated generally at 2. The oxygen sensing element 2 has a tubular main body 4 of a selected oxygen-ion conductive solid electrolyte, which is closed at its one end and open at the other end. The tubular main body 4 has a measuring electrode formed on its outer surface, and a reference electrode formed on its inner surface. The reference electrode is adapted to be exposed to a reference gas such as an ambient air or atmosphere.

Figure 1B:
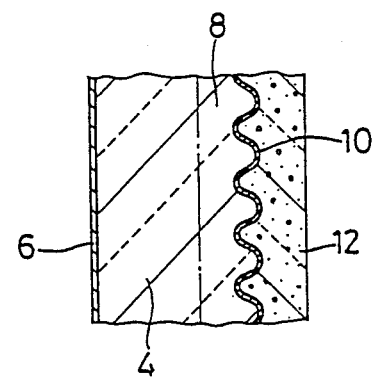
FIG. 1(b) is a fragmentary enlarged view of a portion of the sensing element indicated at A in FIG. 1(a)

Described more specifically by reference to the fragmentary enlarged view of FIG. 1(b), the reference electrode indicated at 6 is formed on the inner surface of the tubular main body 4, while an undulated layer 8 is formed on the outer surface of the main body 4, as an integral part of the main body 4. The measuring electrode, which is indicated at 10, is formed on the undulated surface of the undulated layer 8. The measuring electrode 10 is covered by a porous ceramic protective coating 12 which has a suitable thickness.

EXAMPLES

To further clarify the concept of the present invention, some typical examples of the invention will be illustrated and described. However, it is to be understood that the invention is by no means limited to the details of the illustrated examples, but may be embodied with various changes and modifications which may occur to those skilled in the art, without departing from the spirit of the invention.

Initially, 3 parts by weight of $Al_2O_3$ and 1 part by weight of $SiO_2$ were added as sintering aids to 100 parts by weight of a mixture consisting of 94 mol % of $ZrO_2$ and 6 mol % of $Y_2O_3$. As a result, an intimate mixture of $ZrO_2$, $Y_2O_3$, $Al_2O_3$ and $SiO_2$ was prepared. The intimate mixture was calcined for three hours at 1000° C. The calcined mixture was wet-crushed to an average particle size of 0.7 microns, by a ball mill for 20 hours, whereby a standard slurry was obtained. Polyvinyl alcohol was added as a binder to the obtained standard slurry such that the polyvinyl alcohol was 1% by weight of the solid portion of the slurry. Then, the slurry was processed by a spray drier so as to prepare a standard solid electrolyte material in the form of granules whose grain size is about 50 microns.

Figure 2:
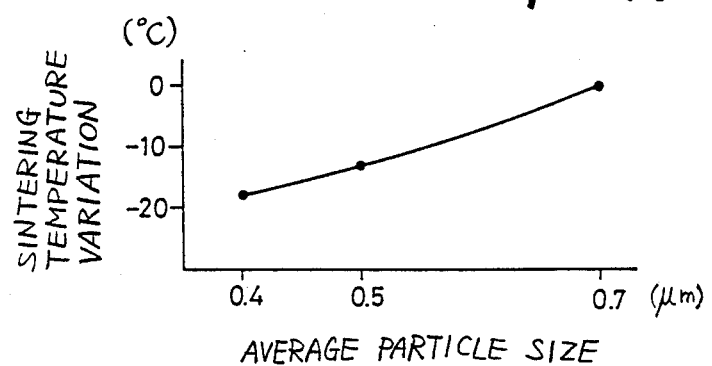
FIG. 2 through FIG. 6 are graphs which respectively show changes in the sintering temperature of solid electrolyte materials, in relation to an average particle size and a dry-crushing time of the materials, a rubber-press pressure applied to the materials, and amounts of $Y_2O_3$ and $SiO_2$ added to the materials.
Figure 3:
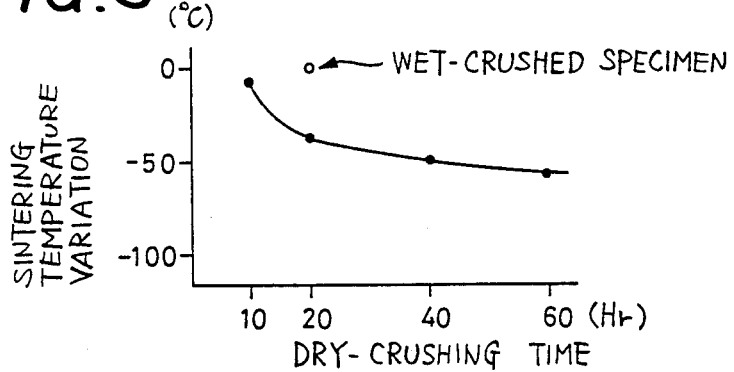
Figure 4:
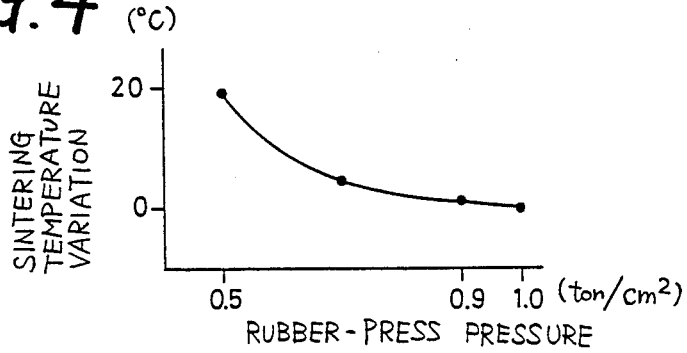

In order to obtain various other solid electrolyte specimens for comparison with the above standard solid electrolyte material, five process step conditions or parameters were changed from the standard conditions indicated above. These five process step parameters are: (a) particle size (FIG. 2); (b) crushing method (FIG. 3); (c) rubber-press pressure (FIG. 4); (d) content of $Y_2O_3$ (FIG. 5); and (e) content of $SiO_2$ (FIG. 6). Relationships between the sintering temperature of the prepared various solid electrolyte specimens and the value of each of the five process step parameters used are illustrated in FIGS. 2–6.

To evaluate the sinterability of the various solid electrolyte specimens, tablets having a diameter of 20 mm and a thickness of 3 mm were formed from each solid electrolyte specimen, by a rubber press under a pressure of 1 ton/cm². The formed tablets of each specimen were fired at different temperatures (for the same time period of five hours). Open porosities or ratios of open pores of the fired tablets were measured. The term "sintering temperature" used herein is interpreted to mean a firing temperature which gives the fired tablet specimen an open porosity of less than 0.20%. Each of the graphs in FIGS. 2 through 6 shows a variation in the sintering temperature of the prepared tablet specimens with respect to the sintering temperature of the standard tablet specimen which was prepared from the standard solid electrolyte material as described above.

(a) Sintering Temperature Varying with Average Particle Size (FIG. 2)

Average particle size of the solid electrolyte specimens just after the wet-crushing was changed from the standard 0.7 micron to lower values, by changing the wet-crushing time. FIG. 2 shows that the sintering temperature was lowered with a decrease in the average particle size of the powder. Namely, it was found that the sintering temperature was lowered as the average particle size is reduced.

(b) Sintering Temperature Varying with Crushing Method (FIG. 3)

The calcined solid electrolyte material was dry-crushed by a ball mill, rather than wet-crushed. Different dry-crushed powder specimens were prepared by changing the crushing time. FIG. 3 shows that the sintering temperature of the dry-crushed specimens was lower than that of the wet-crushed specimens. FIG. 3 further shows that the sintering temperature was lowered as a function of the dry-crushing time. Thus, it was found to be possible to adjust the sinterability of the solid electrolyte material by selecting the wet- or dry-crushing method, and/or changing the dry-crushing time.

(c) Sintering Temperature Varying With Forming Pressure (FIG. 4)

The pressure at which the above-indicated tablets were formed on the rubber press was changed from the standard 1.0 ton/cm² to different lower values as indicated in FIG. 4. The graph of this figure shows that the sintering temperature was elevated as the rubber press pressure was lowered.

Figure 5:
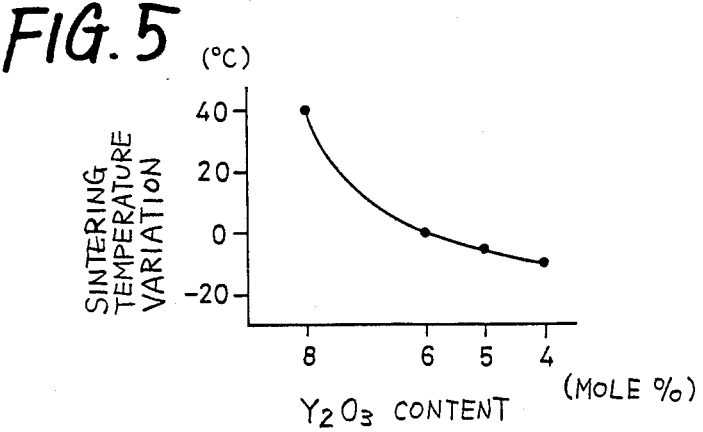
Figure 6:
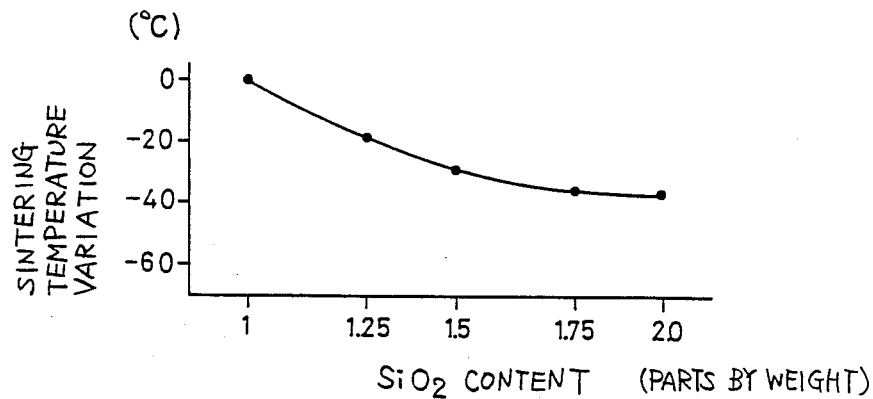

(d) Sintering Temperature Varying with $Y_2O_3$ Stabilizer Content (FIG. 5)

The content of yttria ($Y_2O_3$) used as a stabilizer for the zirconia ($ZrO_2$) solid electrolyte was changed from the standard 6 mol % to different values as indicated in FIG. 5. The graph of this figure shows that the sintering temperature was increased with the content of the stabilizer.

(e) Sintering Temperature Varying with SiO₂ Sintering Aid Content (FIG. 6)

The content of silicon dioxide ($SiO_2$) used as a sintering aid for the $ZrO_2$-$Y_2O_3$ solid electrolyte material was changed from the standard 1 weight % to different values as indicated in FIG. 6. The graph of this figure shows that the sintering temperature was lowered with an increase in the content of the sintering aid. Namely, it was found that the sinterability of the solid electrolyte material was improved as the content of the sintering aid was increased.

Unfired tubular main bodies as shown in FIG. 1 for an oxygen sensing element were prepared in the following procedure. Pressed bodies were formed by a rubber press, by using the standard solid electrolyte material prepared in the manner previously described. The outer surface of the pressed bodies was ground to the predetermined outer diameter of the unfired main body (4). In the meantime, different solid electrolyte powder specimens for unfired undulated layers (8) were prepared by changing the wet-crushing or dry-crushing conditions, so that the obtained powder specimens have different sintering temperatures lower than that of the solid electrolyte material for the main body (4). Slurry specimens were prepared by adding a binder (PVA or methyl cellulose) and water to the powder specimens for the undulated layer (8). The prepared slurries were applied to the ground outer surface of the unfired tubular main bodies (4), by spraying or dipping method, so that the unfired undulated layer (8) having a predetermined thickness is formed. Each unfired main body (4) with the unfired undulated layer (8) formed thereon was dried at 100° C. for one hour, and was then heated to 500° C. in order to remove the binder. Subsequently, the thus treated structure (4, 8) was fired at its selected sintering temperature for five hours.

In the manner described above, different specimens of the main body 4 with the integral undulated layer 8 were prepared. To check the fired condition of the outer surface of each main body 40, i.e., the undulated layer 8, each specimen was observed in cross section by SEM photography (by a scanning electron microscope). On the inner and outer surfaces of the fired structure, platinum electrodes were formed and fired in an ordinary manner. Described more particularly, the measuring electrode 10 was formed on the undulated layer 8, while the reference electrode 6 was formed on the inner surface of the main body 4. Then, the spinel ceramic protective coating 12 was formed by spray coating technique on the undulated layer 8. Thus, different oxygen sensing elements 2 as shown in FIG. 1 were prepared.

Figure 8:
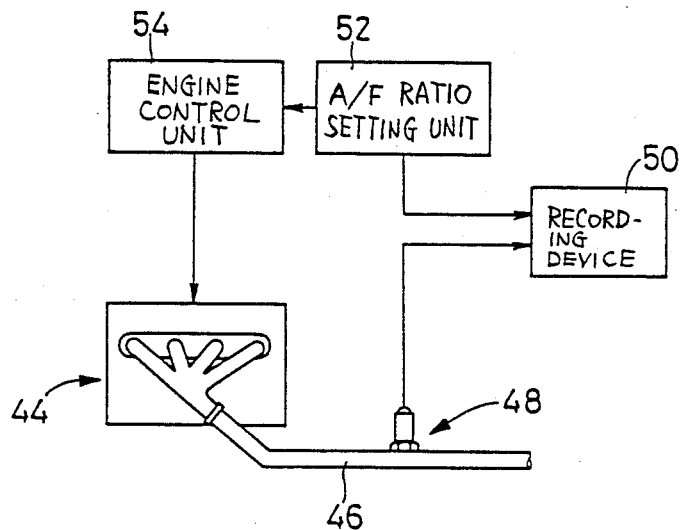
FIG. 8 is an explanatory view showing an arrangement for measuring an operating response time of the oxygen sensing element.
Figure 7:
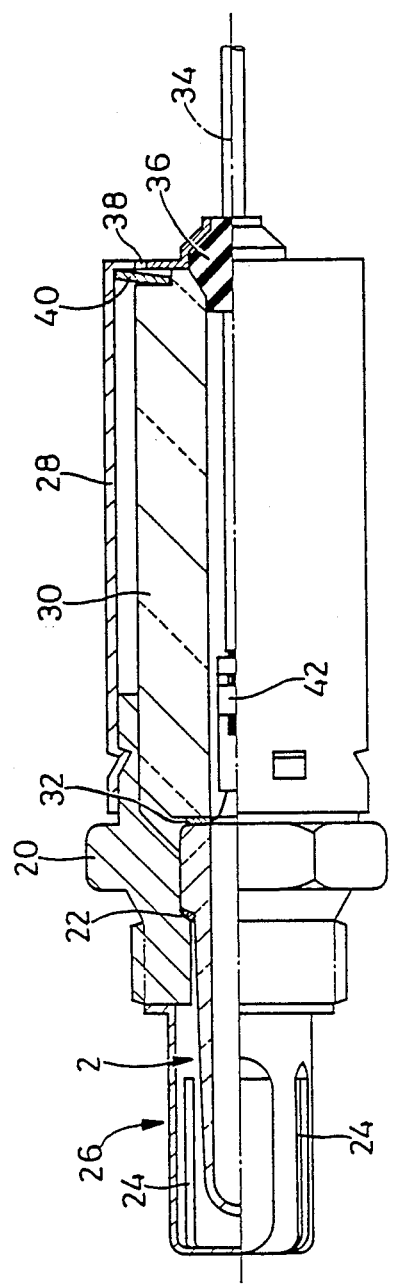
FIG. 7 is an elevational view partly in longitudinal cross section of an assembly in which is incorporated the oxygen sensing element of FIG. 1.

Each of the prepared sensing elements 2 was built in an oxygen sensor as indicated in FIG. 7, and the oxygen sensor was attached to an engine 44 as illustrated in FIG. 8, to check each oxygen sensing element for its operating response.

In FIG. 7, reference numeral 20 designates a housing to which the measuring electrode 10 is electrically connected via a contact packing 22. To the inner end of this housing 20, there is secured a protective covering 26 which is located within a stream of a measurement gas. The oxygen sensing element 2 is accommodated within the protective covering 26, so that the sensing element is exposed to the measurement gas, through a louver 24 formed on the protective covering 26. To the outer end of the housing 20, there is fixed a cap 28 in which an insulating member 30 is disposed to hold the oxygen sensing element 2 in pressed contact therewith. A signal electrode 32 is disposed between the sensing element 2 and the insulating member 30. A lead wire 34 is connected via the signal electrode 32 to the reference electrode 6 formed on the inner surface of the sensing element 2. Reference numeral 36 indicates a rubber plug through which the lead wire 34 extends, and reference numerals 38, 40 and 42 respectively designate an air inlet aperture, a coned-disc spring (belleville spring), and a connector which is caulked for electrical connection of the lead wire 34.

Referring to FIG. 8, the oxygen sensor incorporating each sensing element 2 as shown in FIG. 7 is indicated at 48. The oxygen sensor 48 was installed on an exhaust pipe 46 connected to the engine 44. An output of the oxygen sensor 48 is applied to a recording device 50. The recording device 50 also receives a changeover signal from an A/F-ratio setting unit 52. The changeover signal is indicative of a point of time at which a command to be applied from the setting unit 52 to an engine control unit 54 is changed. Namely, the command from the setting unit 52 is indicative of an A/F ratio of an air-fuel mixture to be supplied to the engine 44, so that the engine 44 is controlled according to a signal from the control unit 54.

An operating response time $T_{RL}$ (t msec.) of the prepared various sensing elements 2 was measured under the conditions specified below and shown in FIG. 9.

Conditions under which the response time was measured

Gasoline engine 44: 4-cylinder engine having 1500 -cc displacement
Engine speed: 1200 rpm
Exhaust gas temp.: 450° C.±30° C.

Figure 9:
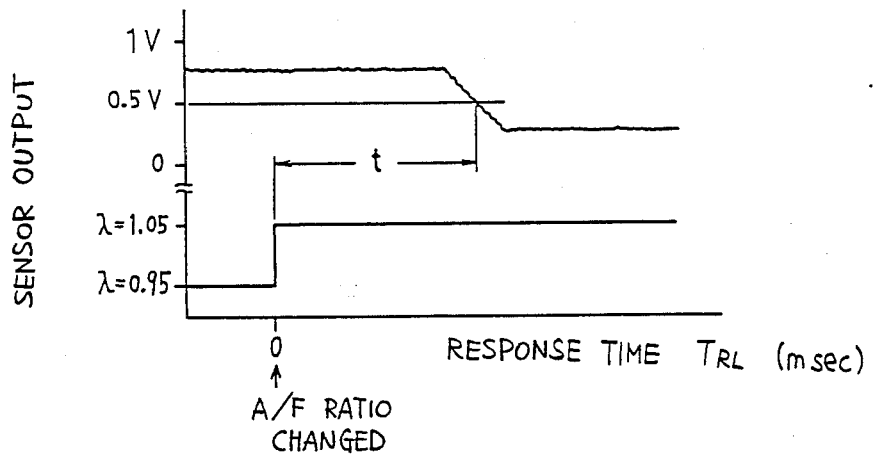
FIG. 9 is a graph showing a condition in which the response time is measured according to the arrangement of FIG. 8.

In the measurement, the response time (t msec.) is a time between a moment when an excess air factor λ determined by the commanded A/F ratio was changed from 0.95 to 1.05, and a moment when the output of the oxygen sensor 48 was lowered from 1V down to 0.5V, as illustrated in FIG. 9. The excess air factor λ is a ratio of an amount of air supplied to the engine 44 per unit volume of the fuel, to an amount of air which corresponds to the stoichiometric A/F ratio.

Figure 10:
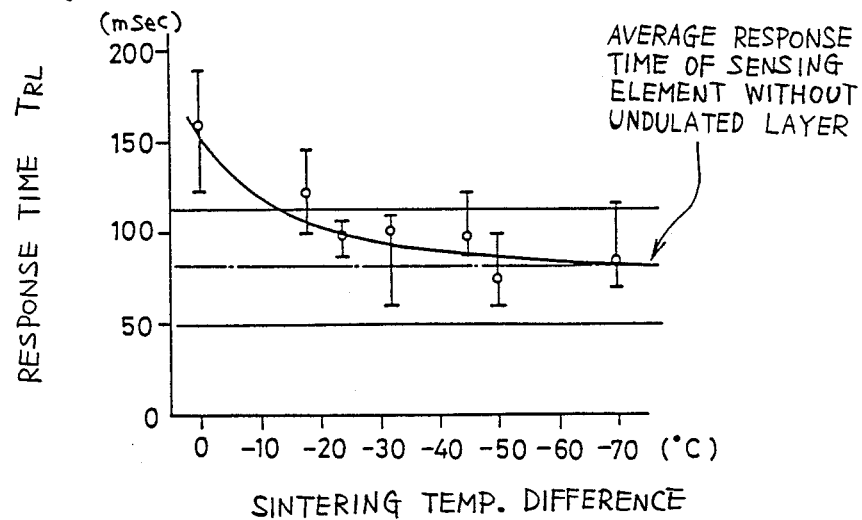
FIG. 10 is a graphical representation indicating a relationship between a difference in the sintering temperature of the materials for the main body and undulated layer of the sensing element, and the response time of the sensing element.

The thus measured response times $T_{RL}$ (t msec.) of the individual sensing elements 2 are shown in FIG. 10. In the graph, a difference in the sintering temperature between the solid electrolyte material for the undulated layer 8 and the standard solid electrolyte for the main body 4 is taken along the abscissa. It is noted that the sintering temperature of the undulated layer 8 is lower than that of the main body 4, and the difference is therefore a negative value. It will be understood from the graph in FIG. 10 that the response time of the sensing elements 2 decreases with an increase in the difference in the sintering temperature between the undulated layer 8 and the main body 4. That is, the operating response is improved as the sintering temperature difference increases.

Drop tests were conducted on the prepared sensing elements, in order to check the adhesion between the main body 4 and the undulated layer 8. The adhesion was analyzed by observing whether the undulated layer 8 suffered from a peel-off or flake-off trouble when the sensing element 2 was dropped. The results are indicated in the following table. In the table, mark "x" indicates the occurrence of a considerable degree of peel-off of the undulated layer 8, while mark "Δ" indicates the occurrence of a slight degree of peel-off of the same. Mark "o" indicates that the undulated layer 8 did not suffer from a peel-off defect.

|  | Sintering Temperature Difference (°C.) | | | | | | |
| --- | --- | --- | --- | --- | --- | --- | --- |
|  | 0 | −15 | −20 | −30 | −40 | −50 | −70 |
| Adhesion of Undulated Layer 8 | x | x | Δ | o | o | o | o |

It will be also understood that the peel-off of the undulated layer 8 did not occur, i.e., the undulated layer 8 demonstrated a considerably high degree of adhesiveness to the main body 4, where the difference in the sintering temperature of the solid electrolyte material for the undulated layer 8 from that of the main body 4 exceeds −30° C.

In the instant examples, the unfired undulated layers 8 of selected solid electrolyte materials were applied by spray coating method to the formed unfired main bodies 4. However, it is possible to pre-fire the unfired main bodies 4 at a suitable temperature lower than its final sintering temperature, before the unfired undulated layers 8 are applied thereto. In this case, the entire structures 4, 8 obtained by applying the unfired undulated layers 8 to the respective fired main bodies 4 are fired at the sintering temperature selected for the main bodies. If this pre-firing of the unfired main body 4 is effected, it is preferred that the solid electrolyte material for the undulated layer 8 have a sintering temperature which is lower than that of a solid electrolyte material that is used for the undulated layer 8 where the pre-firing of the main body 4 is not conducted. For example, in a case where the unfired main body 4 has a sintering temperature of 1480° C. and is pre-fired at 1150° C. it is preferred that the solid electrolyte material for the undulated layer 8 applied to the pre-fired main body 4 have a sintering temperature which is at least about 30° C. lower than that of a solid electrolyte material used for the undulated layer 8 applied to an unfired main body 4 which has a sintering temperature of 1480° C. and is not pre-fired. By so determining the solid electrolyte material for the undulated layer 8, the fired undulated layer 8 can be given an improved density, and at the same time the fired undulated layer 8 can be more fully integrated with the fired main body 4.

What is claimed is:

1. A method of producing a sensing element of an oxygen sensor which includes a main body made of an oxygen-ion conductive solid electrolyte, an undulated layer formed on said main body, a measuring electrode formed on said undulated layer for exposure to a measurement gas, and a porous protective coating which covers said measuring electrode, said method comprising the steps of:

preparing a solid electrolyte material which has a higher degree of sinterability than said oxygen-ion conductive solid electrolyte of said main body of the sensing element;

forming an unfired layer for said undulated layer on a selected portion of an unfired body for said main body, by using the prepared solid electrolyte material;

determining firing conditions for said unfired body for said main body; and firing the formed unfired layer for said undulated layer, together with said unfired body for said main body, under the determined firing conditions, to thereby produce said sensing element which has said undulated layer as an integral part of said main body.

2. A method of producing a sensing element according to claim 1, wherein said solid electrolyte material for said undulated layer has an average particle size smaller than that of said oxygen-ion conductive solid electrolyte of said main body of the sensing element.

3. A method of producing a sensing element according to claim 1, wherein said solid electrolyte material for said undulated layer consists of a dry-crushed powder.

4. A method of producing a sensing element according to claim 1, wherein said oxygen-ion conductive solid electrolyte of said main body of the sensing element substantially consists of a fully or partially stabilized zirconia ceramic which includes a stabilizer, and said undulated layer is formed of a zirconia ceramic which includes a stabilizer in an amount smaller than that included in said solid electrolyte of said main body.

5. A method of producing a sensing element according to claim 4, wherein said stabilizer comprises a stabilizing agent selected from the group which consists of yttria, calcia, magnesia and ytterbium oxide.

6. A method of producing a sensing element according to claim 4, wherein said stabilizer consists of yttria.

* * * * *